United States Patent [19]

Robbins et al.

[11] Patent Number: 4,861,919

[45] Date of Patent: Aug. 29, 1989

[54] COUNTERCURRENT MULTI-STAGE WATER CRYSTALLIZATION OF AROMATIC COMPOUNDS

[75] Inventors: Lanny A. Robbins, Midland, Mich.; Ben B. Gammill, Angleton, Tex.

[73] Assignee: The Dow Chemical Company, Midland, Mich.

[21] Appl. No.: 161,589

[22] Filed: Feb. 29, 1988

[51] Int. Cl.$^4$ .................... C07B 63/00; C07C 37/84; C07C 39/06
[52] U.S. Cl. ................................................ 568/724
[58] Field of Search .......................... 260/707; 568/724

[56] References Cited

U.S. PATENT DOCUMENTS

| | | | |
|---|---|---|---|
| 3,227,183 | 10/1966 | Heller et al. | 568/724 |
| 3,326,986 | 6/1967 | Dugan et al. | 568/724 |
| 3,919,330 | 11/1975 | Kwantes et al. | 260/619 R |
| 4,079,087 | 3/1978 | Sun | 260/619 A |
| 4,113,974 | 9/1978 | Mark et al. | 568/750 |
| 4,212,997 | 7/1980 | Adams et al. | 568/724 |
| 4,408,087 | 10/1983 | Li | 568/724 |
| 4,447,655 | 5/1984 | Mendiratta | 568/724 |
| 4,461,915 | 7/1984 | Mendiratta et al. | 568/724 |
| 4,507,509 | 3/1985 | Mendiratta et al. | 568/724 |
| 4,529,823 | 7/1985 | Mendiratta | 568/724 |
| 4,533,764 | 8/1985 | Chang et al. | 568/724 |
| 4,558,414 | 5/1986 | Takegami et al. | 23/295 R |
| 4,740,635 | 4/1988 | Gomes de Matos et al. | 568/724 |

*Primary Examiner*—Mary C. Lee
*Assistant Examiner*—MarySue Howard
*Attorney, Agent, or Firm*—Paula S. Ruhr

[57] ABSTRACT

A process for the purification of an aromatic compound, e.g. isopropylidenediphenol, comprising using a multi-stage countercurrent process wherein the crystals are melted by the addition of heat and water prior to each crystallization step and wherein one crystallization is accomplished at a pre-selected low temperature.

8 Claims, 1 Drawing Sheet

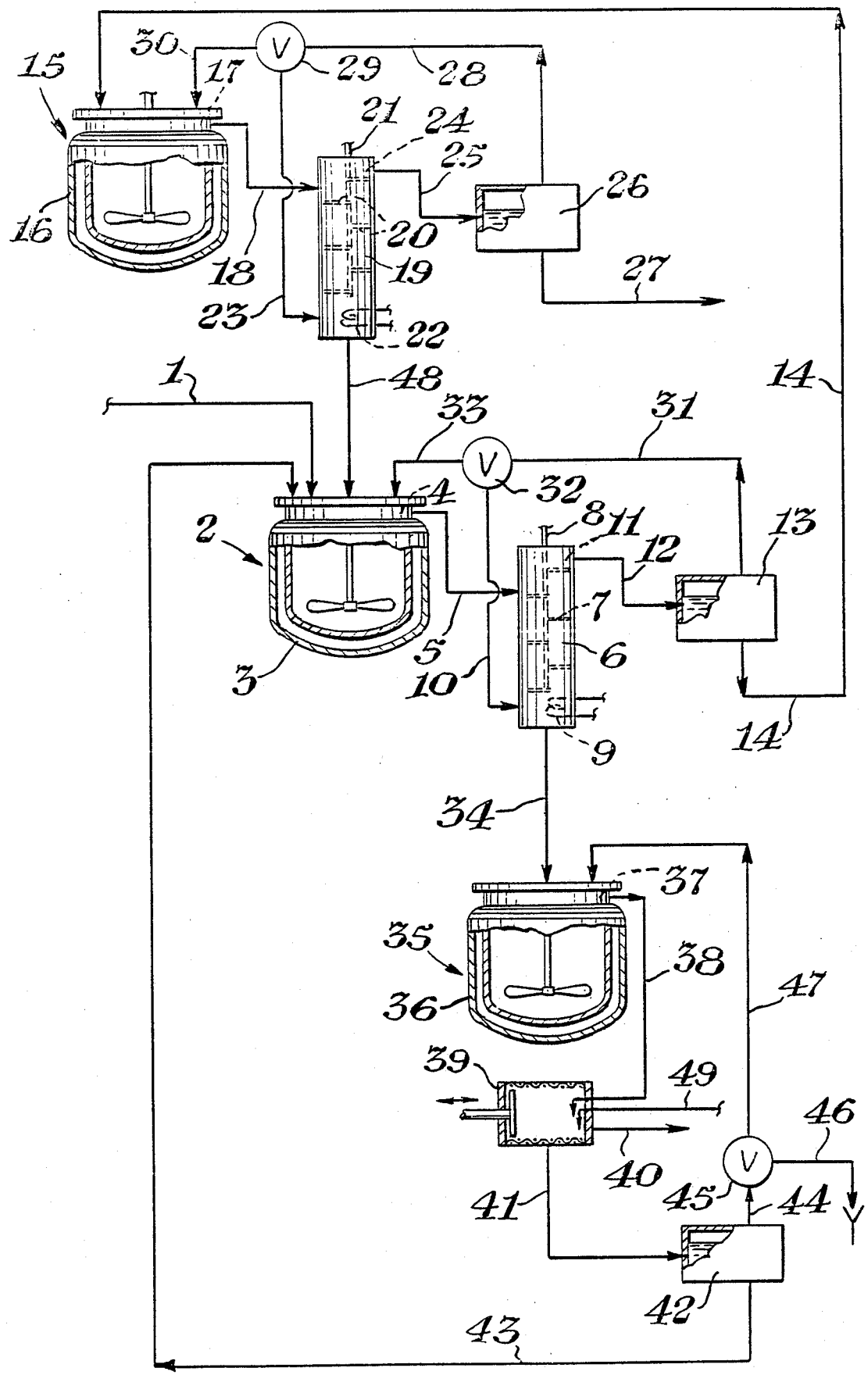

COUNTERCURRENT MULTI-STAGE WATER CRYSTALLIZATION OF AROMATIC COMPOUNDS

BACKGROUND OF THE INVENTION

This invention relates to processes for the purification of aromatic compounds, particularly bisphenols.

Bisphenols are valuable compounds useful in the preparation of epoxy resins and polycarbonates. High quality epoxy resins, and particularly polycarbonates, require especially pure bisphenols for use in their preparation. Known processes for the production of bisphenols produce bisphenols having certain impurities including isomers, analogs and homologs. Therefore, it is necessary to have processes for the purification of the crude product. The purification of the crude product often proves difficult since the common impurities frequently have characteristics very similar to the desired compound.

Numerous processes exist for the purification of bisphenols in general and particularly for the purification of p,p'-isopropylidenediphenol. U.S. Pat. No. 3,919,330 discloses a purification process wherein crude isopropylidenediphenol crystals are dissolved in an organic solvent. Water is then added, the solution is cooled, p,p'-isopropylidenediphenol crystallizes and the crystals are then separated by filtration or centrifugation. Another process is described in U.S. Pat. No. 4,354,046 where it is taught to crystallize a bisphenol from a single liquid phase comprising water, the bisphenol and an organic solvent. The mother liquor is stripped of solvent and water and mixed with phenol. A cation-exchange resin is used to convert the impurities to the desired product and the phenol is recycled. It is also known to purify p,p'-isopropylidenediphenol by using an aqueous alkaline solution (U.S. Pat. No. 4,507,509). Another process for the purification of bisphenols is taught in U.S. Pat. No. 2,959,622 where it is taught to wash the crude bisphenol with water, neutralize it with an alkaline solution and dissolve the crystals in hot water and an immiscible organic solvent. The organic phase is then cooled to recover the product. U.S. Pat. No. 4,461,915 teaches that p,p'-isopropylidenediphenol may be purified by mixing the molten isopropylidenediphenol with water, crystallizing the mixture and then washing the crystals with an organic solvent.

Other methods of purifying bisphenols include contacting bisphenol crystals in water with an organic washing solvent in a continuous, multi-stage, countercurrent extraction column (U.S. Pat. No 4,447,655). A method of purification of a multi-component molten mixture using a countercurrent, cooling multi-stage crystallizer/purifier is described in European Patent Application No. 0 105 524A2.

In each of these processes for the purification of bisphenols, a major goal is to produce bisphenols of high purity in high yields. However, these goals are not always met and it is frequently necessary to sacrifice high yields to obtain high purity or vice versa. In addition, many of the existing methods for the purification of bisphenols require the use of organic solvents which may be flammable or toxic. What is needed is a method for obtaining high purity bisphenols in high yields while avoiding the use of organic solvents.

SUMMARY OF THE INVENTION

The invention is a multi-stage, countercurrent process for the removal of impurities from a crude aromatic compound contaminated by one or more related congeneric impurities, the process comprising subjecting the crude aromatic compound to two or more cycles of crystallization and purification followed by a final crystallization step. The process cycles are characterized by
 (1) melting the aromatic compound crystals prior to each crystallization by the addition of heat and water and in the absence of an organic solvent;
 (2) conducting one crystallization step at a low temperature pre-selected to increase recovery of the aromatic compound;
 (3) separating water and oil which remain after each of the purification steps of the process and after the final crystallization step, and
   (a) recycling the separated water to the crystallization and purification step(s), and
   (b) recycling the separated oil to be recrystallized.
The final crystallization step consists essentially of separating the product crystals from the oil and water and drying the crystals without further purification.

BRIEF DESCRIPTION OF THE DRAWING

The drawing is a schematic representation of one embodiment of the process of this invention. It shows a process in which there are two cycles of crystallization and purification followed by a final crystallization step.

DETAILED DESCRIPTION OF THE INVENTION

The particular nature of the apparatus to be used in the practice of this invention is not critical. The invention can be practiced using several individual crystallizers, purifiers, liquid/oil separators and at least one crystal/liquid separator. It is preferred to use adiabatic, evaporatively cooled, mixed suspension crystallizers. As purifiers, it is preferred to use countercurrent wash columns with heating elements and water injection ports at the bottom of each column. The preferred liquid/oil separators are conventional gravity decanters and it is preferred to use a centrifuge to separate the crystal and liquid. The individual units are connected in series with a purifier being placed between each pair of crystallizers. Any number of units which will result in the purification of the bisphenol may be used.

The impurities which may be removed by the process of this invention are those which are formed during production of the desired aromatic compound. These congeneric impurities typically include, for example, isomers and homologs of the desired aromatic compound. For example, when p,p',isopropylidenediphenol is the desired compound, the impurities may include o,p'-isopropylidenediphenol (the o,p'-isomer), trishydroxyphenyl compounds and various other contaminants formed during the production of p,p'-isopropylidenediphenol.

The aromatic compounds which may be effectively treated to remove impurities by the process of this invention are those which have freezing points which are lowered by mixing water with the molten aromatic compound prior to crystallization. An illustrative, but non-limiting, example of such compounds is p,'-isopropylidenediphenol, Bisphenol A. The freezing point of pure p,p'-isopropylidenediphenol mixed with water is approximately 100° C. while pure p,p'-isopropylidenediphenol alone freezes at about 153° C. Thus, by mixing the molten p,p'-isopropylidenediphenol with water, the p,p'-isopropylidenediphenol may be melted at a much lower temperature than would be possible without the water present. In this way, the high temperatures which lead to undesirable discolorization of the p,p'-isopropylidenediphenol can be avoided.

In the process of this invention, the purification step comprises washing the crystals of the aromatic compound countercurrently with a mixture of the molten compound and water. This is accomplished as the crystals move down a purifier while the molten compound and water reflux up from the bottom of the purifier. The crystals are melted as they reach the bottom of the purifier by the addition of heat and water. No additional solvent is added. The temperature at which the crystals are melted depends on the compound being purified and is selected to be approximately the freezing point of the mother liquor. In the case of p,p'-isopropylidenediphenol, the crystals are melted at a temperature of about 100° C.

The temperature at which each of the crystallizers is operated is selected depending on the purity of the compound being crystallized in the particular crystallizer. The freezing point of the compound being crystallized will vary depending on the percentage of impurities present. For example, p,p'-isopropylidenediphenol under water that is essentially pure melts at between about 99.9° C. and 100.6° C. In contrast, isopropylidenediphenol under water that contains only about 35 percent of the p,p'-isomer with about 65 percent of the o,p'-isomer melts at about 69.0° C. The freezing point of compositions with ratios of para-para and ortho-para isomers varying between those mentioned above also varies between about 69.0° C. and 100.6° C. Thus, at the higher crystallization temperatures needed to obtain relatively pure crystals, the mother liquor will contain correspondingly higher percentages of the desired p,p'-isomer. This results in a low yield of relatively high purity p,p'-isopropylidenediphenol. The use of successive crystallizations followed by washing and remelting at progressively higher temperatures up to the melting point of pure p,p'-isopropylidenediphenol under water increases the purity of the crystals, but also results in relatively low yield of the high purity crystals.

The degree of purity obtained by the practice of this invention is preferably at least about 99.97 percent and more preferably at least about 99.99 percent. If even higher purity is required, it may be obtained by increasing the number cycles of purification and crystallization used.

The yield of the desired compound which may be obtained is also influenced primarily by the temperature at which the crystallizers are operated. As discussed above, in a crystallizer operated at temperatures selected only to result in a high degree of purity, the yield of the desired compound is somewhat low. The use of a pre-selected low temperature crystallizer operated in series with the higher temperature crystallizers results in a substantially higher overall yield being obtained.

The pre-selected low temperature is any temperature which will result in an increased yield. The yield is increased at low temperatures due to the mother liquor containing a low percentage of the desired isomer or compound. It is preferred that the pre-selected low temperature is the lowest temperature at which crystallization of the desired aromatic compound from a mixture of the desired compound and its impurities under water will occur. In a preferred embodiment where it is desired to separate one isomer of the aromatic compound from a mixture of isomers, the preferred pre-selected low temperature is the freezing point of a eutectic mixture of the isomers. In a preferred embodiment of this invention wherein the compound to be purified is isopropylidenediphenol, the pre-selected low temperature is preferably about 70° C. It should be noted that while it is preferred to use the lowest possible pre-selected low temperature to result in the highest yields, other considerations such as process costs or equipment limitations may lead to the use of a somewhat higher pre-selected low temperature.

The crystals obtained from this low temperature crystallization are washed and melted and recrystallized at progressively higher temperatures in order to obtain a higher degree of purity. The overall yield of the desired bisphenol obtained by the practice of this invention is preferably at least about 95 percent and more preferably at least about 98 percent.

The product crystals obtained from the final crystallization are separated from the oil and water remaining after the crystallization by conventional separation techniques. Non-limiting examples of such techniques include filtration, use of cyclones and use of pusher centrifuges. It is preferred to use a pusher centrigue to separate the product crystals from the oil and water. These crystals are dried by conventional techniques without additional purification steps such as washing.

The invention can best be understood by reference to the drawing, FIG. I. It is to be understood that the drawing represents only one embodiment of the invention and is not to be considered as limiting the invention in any way.

Three feed streams, 1, 43 and 48, of a crude molten aromatic compound along with a feed stream 33 of hot water are fed to a stirred mixed suspension crystallizer 2 which is surrounded by a heating jacket 3 and contains a suspension of crystals in water and oil. The crystallizer vessel 2 has a level control 4 which allows the overflow of the suspension to be led via process line 5 to the upper portion of purifier 6 which is raked by arms 7 on rotating shaft 8. The solids move in a downwardly direction. The crystals reaching the bottom of purifier 6 are melted by the addition of hot water from process line 10 and heat from heating element 9. The molten bottoms consist of oil, which is the molten aromatic compound, and water. One of two portions of the molten bottoms refluxes up through purifier 6 to the upper portion of purifier 6 where level control 11 allows the overflow to be removed through process line 12.

The second of the two portions of the molten bottoms from purifier 6 is discharged to process line 34 and carried to stirred crystallizer vessel 35 which is surrounded by heating jacket 36 and contains a suspension of crystals in water and oil. The crystallizer vessel 35 has level control 37 which allows the overflow of the suspension to be led via process line 38 to pusher centrifuge 39. Here the crystals are separated, with the addition of fresh hot water through feed stream 49, from the water and oil and removed as product through process line 40. The water and oil from the pusher centrifuge 39 are taken through process line 41 to separator 42 where the oil is returned via process line 43 to stirred crystallizer vessel 2 for recrystallization and the water is carried away from separator 42 in process line 44. A portion of the water is carried out of the system via process line 46 and the remainder is recycled to stirred crystallizer vessel 35 via process line 47. The amount of water being purged and the amount to be recycled is controlled via valve 45.

The molten overflow in process line 12 is led to separator 13 where the oil and water are separated. The oil is carried via process line 14 to stirred crystallizer vessel 15. The water is carried away from separator 13 via process line 31. Valve 32 controls the amount of water carried via process line 10 to purifier 6 and the amount of water carried via process line 33 to stirred crystallizer vessel 2.

The crystallizer vessel 15 is surrounded by a heating jacket 16 and contains a suspension of crystals in water and oil. The crystallizer vessel 15 has level control 17 which allows the overflow of the suspension to be led via process line 18 to the upper portion of a purifier 19 raked by arms 20 on a rotating shaft 21. The solids move in a downwardly direction. The crystals reaching the bottom of purifier 19 are melted with the addition of hot water from process line 23 and heat from heating element 22. One of two portions of the molten bottoms which consist of oil and water refluxes up through purifier 19 where a level control 24 allows a portion of them to be removed as overflow through process line 25 to separator 26. The oil and water are separated in separator 26 and the oil is purged from the system via process line 27 while the water is carried away from the separator in process line 28. Valve 29 controls the amount of water going via process line 23 to purifier 19 and the amount going via process line 30 to stirred crystallizer vessel 15.

The second of two portions of the molten bottoms which consist of oil and water are removed from the bottom of purifier 19 and carried via process line 48 to stirred crystallizer vessel 2.

The following example is provided for illustrative purposes only and should not be viewed as limiting the invention in any way. Unless stated otherwise, all parts and percentages are given by weight.

EXAMPLE

Purification of Isopropylidenediphenol

This example used the process schematically outlined in FIG. I and can best be understood by reference to the FIG.

A feed stream consisting of molten 97.5 percent p-p'-isopropylidenediphenol with the remaining 2.5 percent being impurities such as the o,p'-isomer, is fed to crystallizer 2 which is operated at 95° C. In addition, hot water and oil which contains 97.0 percent p-p'-isopropylidenediphenol recycled from oil and water separator 42 and the molten crystals from purifier 19 are also fed to the crystallizer. The crystals formed here are taken in an oil and water suspension to a purifier 6 where they are washed and re-melted by the addition of water and heat. A portion of these molten bottoms forms the feed for crystallizer 35 and the remainder is allowed to reflux up through the purifier to wash the new crystals being added at the top of the purifier. The overflow from the purifier 6 which consists of water and oil is separated and the water is used again in crystallizer 2 and purifier 6. The oil which contains about 90 percent p-p'-isopropylidenediphenol is used as feed for crystallizer 15.

Crystallizer 15 is operated at 70° C. and the procedure followed for crystallizer 2 and purifier 6 is repeated using crystallizer 15 and purifier 19 with the following exceptions. The molten bottoms from purifier 19 form a part of the feed for crystallizer 2. When the oil and water overflowing from purifier 19 are separated, the water is used again in purifier 19 and crystallizer 15, but the oil, containing only about 35 percent p,p'-isopropylidenediphenol is removed from the system.

The molten bottoms from the bottom of purifier 6 form the bisphenol feed for crystallizer 35 operated at 98° C. The crystals formed here are separated from an oil and water suspension in pusher centrifuge 39 with the addition of fresh hot water at a temperature of about 100° C. and removed as product crystals without further treatment. The crystals are dried by conventional driers and their purity is measured by gas chromatography. The crystals are found to be 99.99 percent p,p'-isopropylidenediphenol and represent a yield of 98.6 percent based on the amount of 97.5 percent p,p'dd-isopropylidenediphenol feed provided to crystallizer 2 via feed stream 1. The oil and water removed from the crystals is separated and the water is used again in crystallizer 35 and the oil which is 97 percent p,p'-isopropylidenediphenol forms a part of the feed for crystallizer 2.

What is claimed is:

1. A multi-stage, countercurrent process for the removal of impurities from a mixture of bisphenol-A and congeneric impurities contaminated by one or more related congeneric impurities, the process comprising subjecting the crude compound to at least two cycles of crystallization and purification wherein the purification step(s) comprise washing the crystals of the bisphenol-A countercurrently with a mixture of the compound in molten form and water followed by a final crystallization step wherein the cycles comprise
   (1) melting the compound crystals prior to each crystallization by the addition of heat and water and in the absence of an added organic solvent;
   (2) conducting one crystallization step at a low temperature pre-selected to increase recovery of the bisphenol-A;
   (3) conducting at least one crystallization step at a temperature greater than about 95° C.; and
   (4) separating water and oil which remain after each of the purification steps of the process and after the final crystallization step; and
      (a) recycling the separated water to the crystallization and purification step(s); and
      (b) recycling the separated oil to be recrystallized;
   and the final crystallization step consists essentially of separating the crystals from the oil and water and drying the crystals without further purification.

2. The process of claim 1 wherein the pre-selected low temperature is 70° C.

3. The process of claim 2 wherein the p,p'-isopropylidenediphenol obtained is at least about 99.99 percent pure.

4. The process of claim 3 wherein the p,p'-isopropylidenediphenol is obtained in a yield of at least about 98 percent based on the amount of crude p-bisphenol provided.

5. The process of claim 1 comprising subjecting the crude bisphenol-A to two cycles of crystallization and purification followed by a final crystallization step.

6. The process of claim 1 wherein the pre-selected low temperature is the lowest temperature at which the bisphenol-A will crystallize out of a eutectic mixture of the bisphenol-A and its related impurities.

7. The process of claim 1 wherein the purification step is accomplished using a counter-current wash column equipped with a heater and a water inlet.

8. The process of claim 1 wherein the crystallization step(s) is(are) accomplished using an adiabatic, evaporatively cooled, mixed suspension crystallizer(s).

* * * * *